(12) United States Patent
Nita et al.

(10) Patent No.: US 7,621,929 B2
(45) Date of Patent: Nov. 24, 2009

(54) ULTRASOUND CATHETER APPARATUS

(75) Inventors: Henry Nita, Redwood City, CA (US); Jeff Sarge, Fremont, CA (US); Simon Nguyen, San Jose, CA (US)

(73) Assignee: FlowCardia, Inc., Sunnyvale, CA (US)

( * ) Notice: Subject to any disclaimer, the term of this patent is extended or adjusted under 35 U.S.C. 154(b) by 645 days.

(21) Appl. No.: 11/179,829

(22) Filed: Jul. 11, 2005

(65) Prior Publication Data

US 2005/0245951 A1   Nov. 3, 2005

Related U.S. Application Data

(62) Division of application No. 10/375,903, filed on Feb. 26, 2003, now Pat. No. 6,942,677.

(51) Int. Cl.
*A61B 17/32* (2006.01)

(52) U.S. Cl. .......................................... 606/169; 604/22

(58) Field of Classification Search ......... 606/169–174; 604/22, 102, 103, 282, 283; 600/467–470
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,823,717 A | 7/1974 | Pohlman et al. |
| 4,337,090 A | 6/1982 | Harrison |
| 4,505,767 A | 3/1985 | Quin |
| 4,565,589 A | 1/1986 | Harrison |
| 4,665,906 A | 5/1987 | Jervis |
| 4,808,153 A | 2/1989 | Parisi |
| 4,870,953 A | 10/1989 | DonMichael et al. |
| 4,920,954 A | 5/1990 | Alliger et al. |

(Continued)

FOREIGN PATENT DOCUMENTS

DE     2438648 A1    2/1976

(Continued)

OTHER PUBLICATIONS

Calhoun et al., "Electron-beam systems for medical device sterilization" downloaded from web on Oct. 8, 2002 <http://www.devicelink.com/mpb/archive/97/07/002.html> (Jul. 1997) 7 pgs total.

(Continued)

*Primary Examiner*—Kevin T Truong
(74) *Attorney, Agent, or Firm*—Townsend and Townsend and Crew LLP

(57) ABSTRACT

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. At least one absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter.

25 Claims, 5 Drawing Sheets

U.S. PATENT DOCUMENTS

| | | |
|---|---|---|
| 4,924,863 A | 5/1990 | Sterzer |
| 4,936,281 A | 6/1990 | Stasz |
| 5,248,296 A | 9/1993 | Alliger |
| 5,267,954 A | 12/1993 | Nita |
| 5,312,328 A | 5/1994 | Nita et al. |
| 5,326,342 A | 7/1994 | Pflueger et al. |
| 5,342,292 A | 8/1994 | Nita et al. |
| 5,380,274 A | 1/1995 | Nita |
| 5,382,228 A | 1/1995 | Nita et al. |
| 5,397,293 A | 3/1995 | Alliger et al. |
| 5,397,301 A | 3/1995 | Pflueger et al. |
| 5,417,672 A | 5/1995 | Nita et al. |
| 5,540,656 A | 7/1996 | Pflueger et al. |
| 5,542,917 A | 8/1996 | Nita et al. |
| 5,916,192 A | 6/1999 | Nita et al. |
| 5,957,882 A | 9/1999 | Nita et al. |
| 5,989,208 A | 11/1999 | Nita |
| 5,997,497 A | 12/1999 | Nita et al. |
| 6,296,620 B1 | 10/2001 | Gesswein et al. |
| 6,494,891 B1 | 12/2002 | Cornish et al. |
| 6,508,781 B1 | 1/2003 | Brennan et al. |
| 6,855,123 B2 * | 2/2005 | Nita ............................ 604/22 |
| 6,942,677 B2 | 9/2005 | Nita et al. |

FOREIGN PATENT DOCUMENTS

| | | |
|---|---|---|
| DE | 3821836 A1 | 1/1990 |
| EP | 0 316 789 A2 | 5/1989 |
| EP | 0 316 789 A3 | 5/1989 |
| EP | 0 316 789 B1 | 5/1989 |
| WO | WO 87/05739 A1 | 9/1987 |
| WO | WO 89/06515 A1 | 7/1989 |
| WO | WO 90/01300 A1 | 2/1990 |
| WO | WO 97/45078 A | 12/1997 |

OTHER PUBLICATIONS

E-Beam Theory RDI-IBA Technology Group, downloaded from web on Oct. 8, 2002 <http://www.e-beam-rdi/EbeamTheory.htm> 2 pages total.

"Irradiation, biological, and other technologies: E-beam, biological, and sharps treatment systems" Chapter 9: Irradiation, Biological, and Other Technologies, *Non-Incineration Medical Waste Treatment Technologies*, (Aug. 2001), pp. 69-74.

What is electron beam curing? downloaded from web on Nov. 14, 2002 <http://www.ms.ornl.gov/researchgroups/composites/new%20orccmt%20pages/pages/ebwha> 4 pgs total.

EP supplemental Search Report mailed Apr. 29, 2009; Application No. 04711207.3, 3 pages.

* cited by examiner

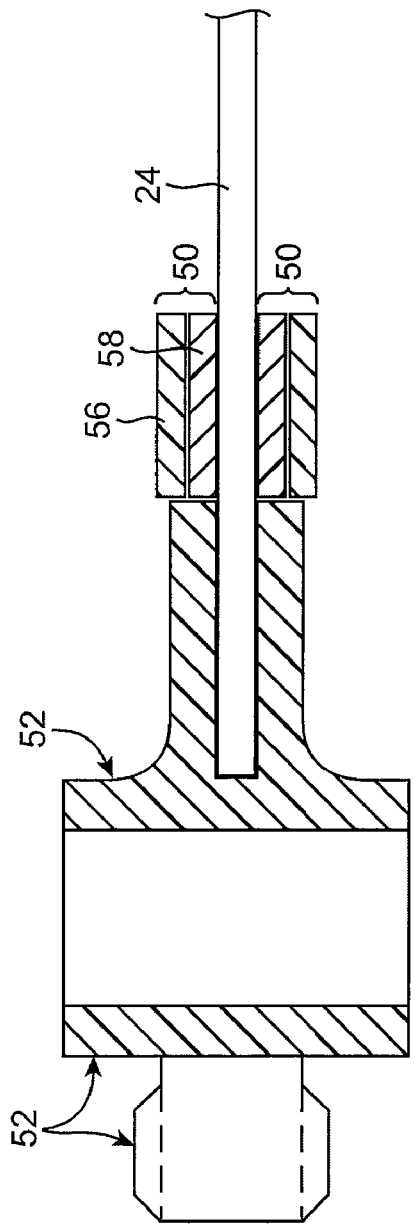
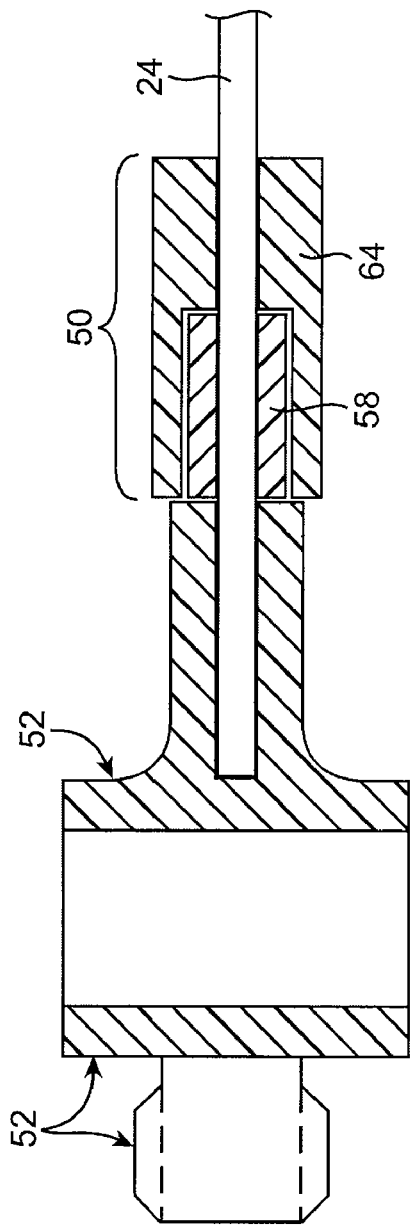
FIG. 4A
FIG. 4B

US 7,621,929 B2

ULTRASOUND CATHETER APPARATUS

This application is a division of U.S. patent application Ser. No. 10/375,903, filed Feb. 26, 2003, and is related to pending U.S. patent application Ser. No. 10/229,371, filed Aug. 26, 2002, entitled "Ultrasound Catheter for Disrupting Blood Vessel Obstructions," the full disclosures of which are hereby incorporated by reference.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al), and 4,920,954 (Alliger, et al.), as well as other patent publications W087-05739 (Cooper), W089-06515 (Bernstein, et al.), W090-0130 (Sonic Needle Corp.), EP, EP316789 (Don Michael, et al.), DE3, 821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions and contractions have both longitudinal and transverse components (relative to an axis of the transducer and the catheter), which are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Due to attenuation of ultrasound energy along the long, thin, ultrasound transmission wire, a sufficient amount of vibrational energy must be applied at the proximal end of the wire to provide a desired amount of energy at the distal end.

An ultrasound transmission wire is usually coupled at its proximal end with the transducer by means of a sonic connector. The sonic connector typically has a significantly larger diameter than that of the ultrasound transmission member, the difference in diameters helping to amplify the vibrational energy being transmitted from the transducer to the transmission wire. This amplification of vibrations, however, creates stress and heat in the transmission wire in an area adjacent its connection with the sonic connector. Stress and heat generated by these amplified vibrations (especially transverse vibrations) significantly reduce the usable life of the ultrasound transmission wire and may cause its premature breakage at or near the point of contact with the sonic connector.

Efforts have been made to reduce transverse vibrations somewhere along the length of an ultrasound transmission member. For example, U.S. Pat. Nos. 5,382,228 and 6,494, 891, both of which issued to an inventor of the present invention and are hereby incorporated by reference, describe mechanisms for absorbing transverse motion of an ultrasound transmission wire. Currently available devices and devices described in the above patents, however, to not reduce stress and/or heat in an ultrasound transmission wire at or near its point of contact with a sonic connector as much as may be desired. As just discussed, this proximal area of the transmission wire may be one of the most vulnerable areas due to its exposure to amplified vibrational energy from the sonic connector.

Therefore, a need exists for an improved ultrasound catheter device and method that provides ablation or disruption of vascular occlusions. Ideally, the ultrasound catheter would include means for reducing heat in the ultrasound transmission wire component of the catheter at or near its coupling with the sonic connector component. Alternatively or additionally, it would also be ideal if transverse vibrations and stress were reduced in a proximal portion of the transmission wire. Such catheter devices would ideally be sufficiently thin and flexible to be advanced through narrow, tortuous vasculature, such as the coronary vasculature, while also being configured to enhance the usable life of the ultrasound transmission wire. At least some of these objectives will be met by the present invention.

BRIEF SUMMARY OF THE INVENTION

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. At least one absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter.

In one aspect of the invention, an ultrasound catheter for disrupting occlusions in blood vessels comprises: an elongate flexible catheter body having a proximal end, a distal end and at least one lumen; an ultrasound transmission member extending longitudinally through the lumen of the catheter body; a sonic connector coupled with a proximal end of the ultrasound transmission member for coupling the ultrasound transmission member with a separate ultrasound generating device; and at least one heat absorbing member coupled with the ultrasound transmission member adjacent the sonic connector. In some embodiments, the heat absorbing member surrounds a portion of the ultrasound transmission member adjacent a distal end of the sonic connector. Optionally, the heat absorbing member includes a bore for receiving the ultrasound transmission member. In some embodiments, such a heat absorbing member is tubular.

In some embodiments, the heat absorbing member contacts a distal end of the sonic connector, while in other embodiments the heat absorbing member may be separated from a distal end of the sonic connector by a distance of a few millimeters. The heat absorbing member may comprise one piece or, in other embodiments, the heat absorbing member may comprise at least two component parts such as at least one absorptive part in contact with the transmission member for absorbing heat and at least one constraining part coupled with the absorptive part for holding the absorptive part in place on the transmission member. In some such embodiments, the constraining part contacts the transmission member and comprises at least one absorptive material for absorbing heat. In various embodiments, the constraining part may either contact a portion of the sonic connector or overlap a portion of the sonic connector. Optionally, at least one of the absorptive part and the constraining part may be capable of absorbing vibrations. In some embodiments, the constraining part comprises a bore for receiving the ultrasound transmission wire, wherein the bore includes a widened portion for receiving the absorptive part. In some embodiments, the constraining part is tubular. Also in some embodiments, the constraining part is coupled with at least one of the absorptive part and the ultrasound transmission wire by at least one of crimping, bonding, fusing or welding.

In other embodiments, the heat absorbing member comprises at least two component parts comprising at least one vibration absorptive part in contact with the transmission member for absorbing vibrations and at least one constraining part coupled with the absorptive part for holding the absorptive part in place on the transmission member and for absorbing heat. In some embodiments, the constraining part contacts a portion of the sonic connector, while in other embodiments it overlaps a portion of the sonic connector. In some embodiments, the constraining part comprises a bore for receiving the ultrasound transmission wire, wherein the bore includes a widened portion for receiving the absorptive part. In such embodiments, the constraining part may sometimes be tubular.

In some embodiments, the heat absorbing member is capable of absorbing vibrations. In other embodiments, the ultrasound catheter further includes a vibrational absorbing member coupled with the ultrasound transmission member for absorbing vibrations. In either case, the heat absorbing member may comprise at least one metal having heat conductivity properties. The metal(s) may include, but are not limited to, aluminum and its alloys, titanium and its alloys, and/or magnesium and its alloys. Finally, in some embodiments the heat absorbing member is coupled with the ultrasound transmission wire by at least one of crimping, bonding, fusing or welding.

In another aspect, an ultrasound catheter for disrupting occlusions in blood vessels includes: an elongate flexible catheter body having a proximal end, a distal end and at least one lumen; an ultrasound transmission member extending longitudinally through the lumen of the catheter body; a sonic connector coupled with a proximal end of the ultrasound transmission member for coupling the ultrasound transmission member with a separate ultrasound generating device; and at least one vibration absorbing member coupled with the ultrasound transmission member adjacent the sonic connector. Any of the features and combinations described for the embodiments above may be equally applied to this aspect of the invention.

In some embodiments, the vibration absorbing member surrounds a portion of the ultrasound transmission member adjacent a distal end of the sonic connector. For example, the vibration absorbing member may include a bore for receiving the ultrasound transmission member. In some embodiments, the vibration absorbing member is tubular. In some embodiments, the vibration absorbing member contacts a distal end of the sonic connector, while in others it is separated from a distal end of the sonic connector by a distance of a few millimeters. For example, in some embodiments, the absorbing member may be separated from the sonic connector by approximately ¼ of a wavelength produced by the ultrasound device.

In some embodiments, the vibration absorbing member comprises at least two component parts, the component parts comprising: at least one absorptive part in contact with the transmission member for absorbing vibrations; and at least one constraining part coupled with the absorptive part for holding the absorptive part in place on the transmission member. In some embodiments, the at least one constraining part contacts the transmission member and comprises at least one absorptive material for absorbing heat. Also in some embodiments, the at least one constraining part contacts or overlaps a portion of the sonic connector. In some embodiments, at least one of the absorptive part and the constraining part is capable of absorbing heat. In some embodiments, the at least one constraining part comprises a bore for receiving the ultrasound transmission wire, wherein the bore includes a widened portion for receiving the absorptive part. In such embodiments, the constraining part may be tubular. The constraining part may be coupled with at least one of the absorptive part and the ultrasound transmission wire by at least one of crimping, bonding, fusing or welding.

In other embodiments, the vibration absorbing member comprises at least two component parts, the component parts comprising: at least one vibration absorptive part in contact with the transmission member for absorbing vibrations; and at least one constraining part coupled with the absorptive part for holding the absorptive part in place on the transmission member and for absorbing heat. The at least one constraining part may contact or overlap a portion of the sonic connector in various embodiments. Optionally, the constraining part may include a bore for receiving the ultrasound transmission wire, wherein the bore includes a widened portion for receiving the absorptive part. In such embodiments, the constraining part may be tubular, for example.

In some embodiments, the vibration absorbing member is capable of absorbing heat. In other embodiments, the ultrasound catheter further includes a heat absorbing member coupled with the ultrasound transmission member for absorbing heat. In some embodiments the vibration absorbing member comprises at least one vibration absorbing material selected from the group consisting of rubbers and polymers. In some embodiments, the vibration absorbing member further comprises at least one metal having heat conductivity properties. For example, such a metal may be selected from the group consisting of aluminum, titanium, and magnesium. In some embodiments, the vibration absorbing member is coupled with the ultrasound transmission wire by at least one of crimping, bonding, fusing or welding.

BRIEF DESCRIPTION OF THE DRAWINGS

FIGS. 4A-4C are cross-sectional views of proximal ends of ultrasound catheters having absorber members according to various embodiments of the invention.

DETAILED DESCRIPTION OF THE INVENTION

Ultrasound catheter devices and methods of the present invention generally provide for ablation and/or disruption of vascular occlusions. An ultrasound transmission member, such as a wire, transmits vibrational energy from an ultrasound transducer to a distal head of the catheter to disrupt vascular occlusions. At least one absorber member is disposed on or around the ultrasound transmission wire at a location adjacent the sonic connector of the catheter. The absorber member absorbs heat, vibrations, and/or the like from the ultrasound transmission wire at or near the area where the transmission wire is coupled with the sonic connector. The absorptive function typically slows the process of wear and tear on the transmission wire, thus extending the useful life of the ultrasound catheter. Although catheters of the invention are described in detail below, for further details reference may be made to U.S. patent application Ser. No. 10/229,371, filed Aug. 26, 2002, which was previously incorporated by reference.

Figure 1:
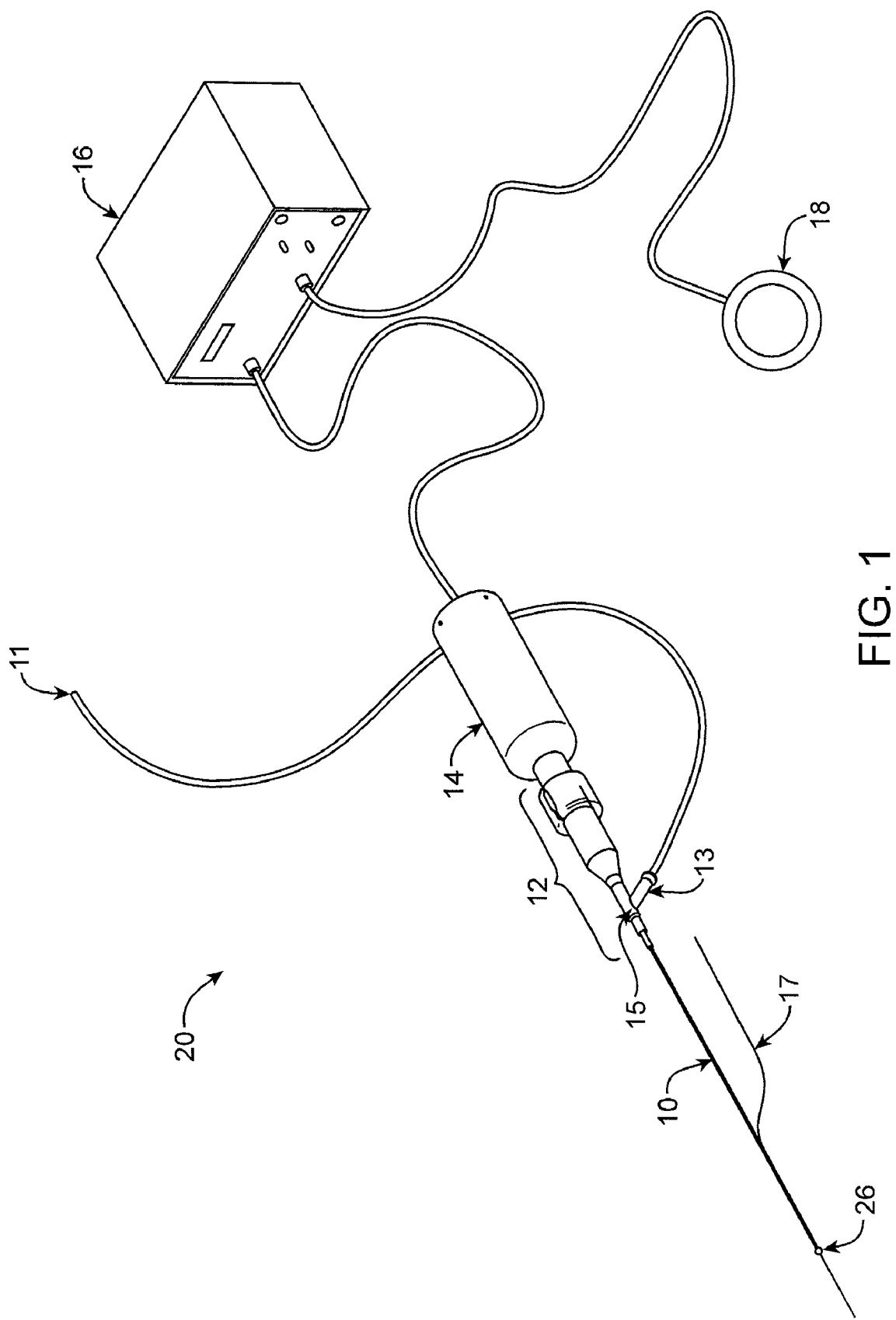
FIG. 1 is a perspective view of an ultrasound catheter system constructed according to the principles of the present invention.

Referring now to FIG. 1, one embodiment of an over-the-wire ultrasound catheter system 20 suitably includes an ultrasound catheter 10, a proximal end connector assembly 12 coupled with catheter 10, an ultrasound transducer 14 coupled with the proximal end of proximal connector assembly 12, and an ultrasound generator 16 with a foot-actuated on/off switch 18, which is operatively coupled with ultrasound transducer 14 to provide ultrasonic energy to transducer 14 and, thus, to ultrasound catheter 10. Generally, catheter 10 will include an ultrasound transmission member, or wire (not shown), for transmitting energy from the transducer 14 to a distal head 26 of the catheter. Proximal connector assembly 12, described more fully below, may have a Y-connector 15 with one or more side-arms 13, for example for providing irrigation fluid via an irrigation tube 11. The catheter 10 may be passed along a guide wire 17 which accesses catheter 10 via a side aperture. The side aperture may be located close to the distal end of catheter 10 or in another embodiment (not shown) close to the proximal end of catheter 10.

Ultrasound catheters 10 of the present invention may be used with any suitable combination of devices, such as any suitable ultrasound transducer 14, ultrasound generator 16, and/or the like. Therefore, exemplary FIG. 1 and any following descriptions of ultrasound catheter apparatus or systems should in no way be interpreted to limit the scope of the present invention as defined in the appended claims. Again, exemplary ultrasound catheters which may incorporate one or more improvements of the present invention are described in previously incorporated U.S. patent application Ser. No. 10/229,371. Other exemplary catheters are described in U.S. patent application Ser. No. 10/345,078, filed on Jan. 14, 2003, entitled "Ultrasound Catheter and Methods for Making and Using Same," by an inventor of the present invention, the full disclosure of which is hereby incorporated by reference. On the other hand, any suitable ultrasound catheter now known or hereafter discovered may be configured to include one or more improvements of the present invention and, thereby, fall within the scope of the invention.

Figure 2:
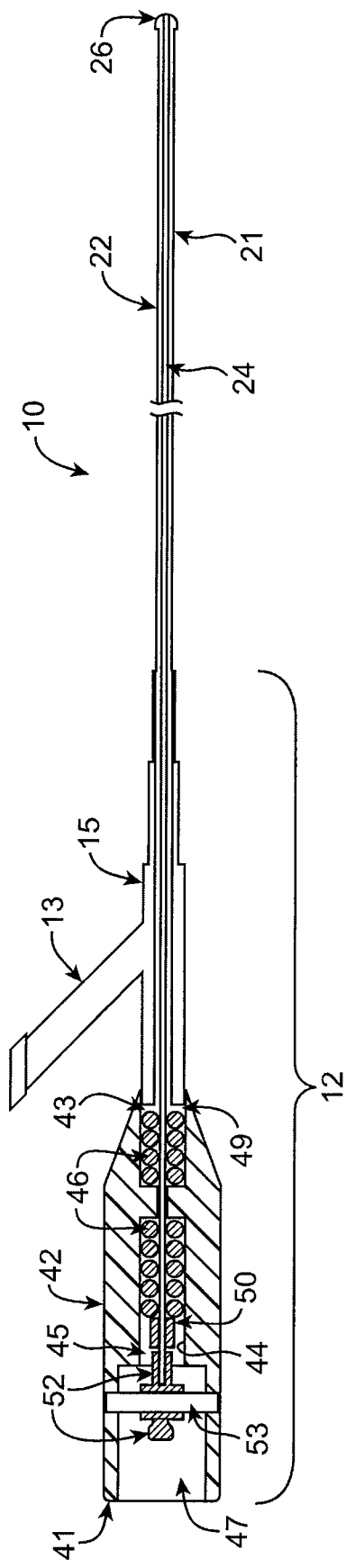
FIG. 2 is a cross-sectional view of an ultrasound catheter having an absorber member according to an embodiment of the present invention.

Referring now to FIGS. 2 and 3, cross-sectional side views of ultrasound catheter 10 and a proximal portion of ultrasound catheter 10 are shown, respectively. Generally, ultrasound catheter 10 suitably includes an elongate catheter body 22 with an ultrasound transmission member 24 disposed longitudinally through its lumen and ending in distal head 26. Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

In most embodiments, ultrasound transmission member 24, wire, or wave guide extends longitudinally through catheter body lumen 21 to transmit ultrasonic energy from ultrasound transducer 14, connected to the proximal end of catheter 10, to the distal end of catheter 10. Ultrasound transmission member 24 may be formed of any material capable of effectively transmitting ultrasonic energy from ultrasound transducer 14 to the distal end of catheter body 22, including but not limited to metals such as pure titanium or aluminum, or titanium or aluminum alloys.

In accordance with one aspect of the invention, all or a portion of ultrasound transmission member 24 may be formed of one or more materials which exhibit superelastic properties. Such material(s) should preferably exhibit superelasticity consistently within the range of temperatures normally encountered by ultrasound transmission member 24 during operation of ultrasound catheter apparatus 10. Specifically, all or part of the ultrasound transmission member 24 may be formed of one or more metal alloys known as "shape memory alloys."

Use of superelastic metal alloys in ultrasound transmission members is described in U.S. Pat. No. 5,267,954, previously incorporated by reference. Examples of superelastic metal alloys which may be used are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries and behavior of specific metal alloys which are superelastic within the temperature range at which the ultrasound transmission member of the present invention operates, any and all of which superelastic metal alloys may be used to form ultrasound transmission member 24 of the present invention.

In many embodiments, ultrasound transmission member 24 includes one or more tapered regions along a portion of its length, towards its distal end. Such a tapered region decreases the distal rigidity of ultrasound transmission member 24, thus amplifying ultrasound energy transmitted along ultrasound transmission member 24 to distal head 26. The tapered region typically divides the transmission member 24 between a proximal portion and a distal portion, which both typically have a larger cross-sectional diameter than the tapered region. A thicker distal portion, for example, may enhance stability of the connection between ultrasound transmission member 24 and distal head 26. Other embodiments are contemplated, however. For example, the tapered region may be positioned at the extreme distal end of transmission member 24. In still other embodiments, ultrasound transmission member 24 may include multiple tapered portions, widened portions and/or the like. Thus, ultrasound transmission member 24 may be configured with any suitable length, combinations of diameters and tapers, or any other suitable shapes, sizes or configurations to advantageously transmit ultrasound energy from transducer 14 to distal tip 26.

In some embodiments ultrasound transmission member 24 may include a low-friction coating or jacket on all or a portion of its outer surface. The coating may be disposed on the outer surface of ultrasound transmission member 24 so as to completely cover ultrasound transmission member 24 along its entire length, or along a discrete region or regions thereof. Such a coating or jacket may comprise a layer of low friction polymer material such as polytetrafluoroethylene (PTFE), TEFLON™ (available from DUPONT, INC., Wilmington, Del.) or other plastic materials such as polyethylene. The coating may be applied as a liquid and subsequently allowed to cure or harden on the surface of ultrasound transmission member 24. Alternatively, the coating may be in the form of an elongate tube, disposable over the outer surface of ultrasound transmission member 24. Generally, the coating serves to prevent or diminish friction between the outer surface of ultrasound transmission member 24 and the adjacent structures of catheter 10 or proximal end connector assembly 12 through which ultrasound transmission member 24 extends.

Figure 3A:
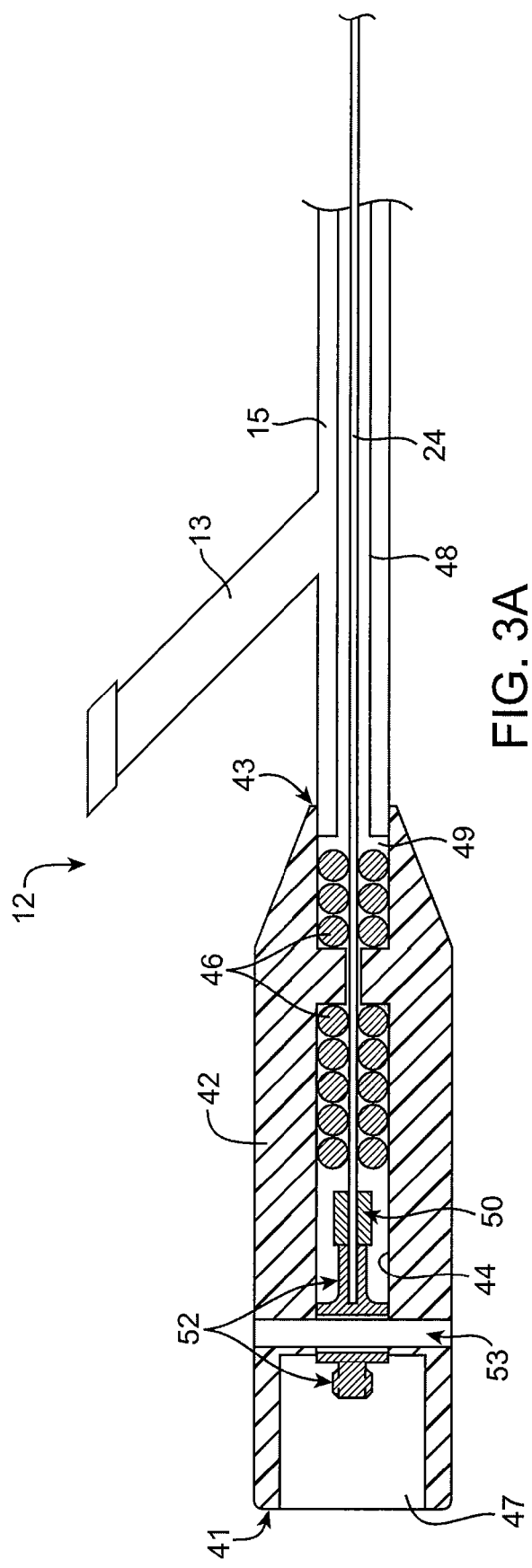
FIG. 3A is a magnified view of a proximal end of an ultrasound catheter as shown in FIG. 2.

With continued reference to FIGS. 2 and 3A, one embodiment of proximal end connector assembly 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector apparatus 12. Generally, proximal segment 47 of bore 44 is configured to allow coupling with ultrasound transducer 14 (not shown) via any suitable coupling means, such as a pressure fit, complementary threads or the like. Proximal segment 47 includes a sonic connector 52 for transmitting vibrational energy from transducer 14 to ultrasound transmission member 24. In some embodiments, sonic connector 52 may be held within housing 42, by means of dowel pin 53. In other embodiments, dowel pin 53 may not be included and sonic connector 52 may be positioned within housing 42 by other means.

Middle segment 45 of bore 44, in some embodiments, may surround a portion of sonic connector 52, while in other embodiments, sonic connector 52 may be housed only within proximal segment 47. Sonic connector 48 is coupled with the distal end of ultrasound transmission member 24 by any suitable means for transmitting ultrasound energy to transmission member 24 from transducer 14. An absorber member 50 is disposed around at least a portion of ultrasound transmission member 24 immediately distal and immediately adjacent to sonic connector 52. Absorber member 50 is described in further detail below, but generally is configured to abut sonic connector 52 to absorb heat and/or transverse vibrations from, and therefore reduce wear and tear on, ultrasound transmission member 24. Optionally, some embodiments further include one or more O-rings 46 distal to absorber member 50 and disposed about ultrasound transmission member 24 for providing further absorption of transverse vibration. Absorber member 50 and O-rings 46 may be used in any number or combination and have and suitable size and configuration, depending on the desired level of vibration absorption or dampening. Alternatively or additionally, other dampening structures may be used. Thus, the invention is not limited to the combination shown in FIG. 2.

Distal segment 49 of bore 44 typically surrounds a portion of ultrasound transmission member 24 and may also contain one or more additional sets of absorber members 46. Distal segment 49 may also contain a portion of a Y-connector 15, which is coupled with the distal end 43 of housing 42 of proximal end connector apparatus 12. Coupling of Y-connector 15 with distal end 43 of proximal end connector assembly 12 may be accomplished via complementary threads, pressure fitting, or any other suitable means. A Y-connector lumen 48 of Y-connector 15 allows passage of ultrasound transmission member 24 and is in communication with the catheter body lumen.

Generally, pressurized fluid such as a coolant liquid may be infused through side-arm 13, through Y-connector lumen 45 and through the catheter body lumen so that it flows out of one or more fluid outflow apertures in distal head. The temperature and flow rate of such coolant liquid may be specifically controlled to maintain the temperature of ultrasound transmission member 24 at a desired temperature within its optimal working range. In particular, in embodiments of the invention wherein ultrasound transmission member 24 is formed of a metal alloy which exhibits optimal physical properties (e.g. super elasticity) within a specific range of temperatures, the temperature and flow rate of coolant liquid infused through fluid infusion side-arm 13 may be specifically controlled to maintain the temperature of ultrasound transmission member 24 within a range of temperatures at which it demonstrates its most desirable physical properties. For example, in embodiments of the invention wherein ultrasound transmission member 24 is formed of a shape memory alloy which exhibits super elasticity when in its martensite state, but which loses super elasticity as it transitions to an austenite state, it will be desirable to adjust the temperature and flow rate of the coolant liquid infused through fluid infusion side-arm 13 so as to maintain the shape memory alloy of ultrasound transmission member 24 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through side-arm 13 will be at such temperature, and will be infused at such rate, as to maintain the shape memory alloy of ultrasound transmission member 24 below its martensite transition temperature.

Figure 3B:
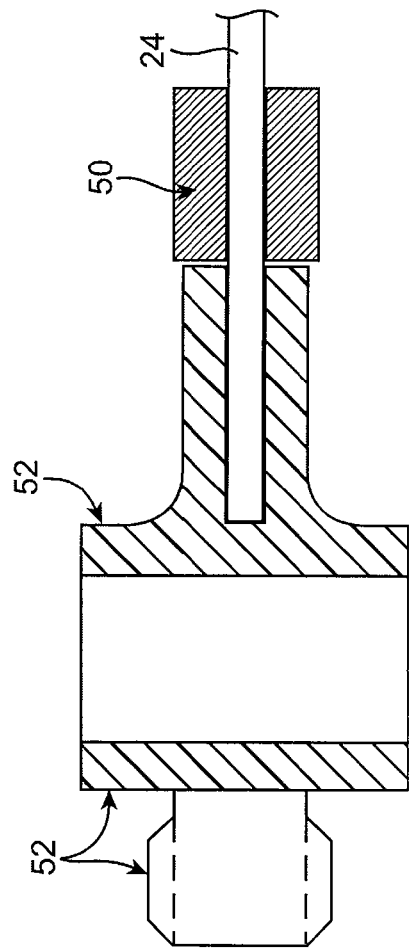
FIG. 3B is a further magnified view of a proximal end of an ultrasound catheter as shown in FIGS. 2 and 3A.

Referring to FIGS. 3A and 3B, one embodiment of absorber member 50 of the present invention is shown disposed about ultrasound transmission wire 24 and immediately adjacent the distal end of sonic connector 52. Generally, absorber member 50 may have any suitable size, shape or configuration, may be made of any suitable material, and may be coupled with ultrasound transmission member 24 by any suitable means to provide for absorption or dampening of heat, transverse vibrations, other unwanted stresses on ultrasound transmission member 24 and/or the like. Typically, absorber member 50 is made from relatively light-weight material(s), so that little or no additional load is placed on the transmission wire. In some embodiments, absorber member 50 comprises one or more materials having heat transfer properties for absorbing heat from ultrasound transmission member 24. Essentially, such an absorber member 50 acts as a heat sink to help prevent ultrasound transmission member from increasing in temperature to a level which may increase wear and tear of transmission member 24. Materials which may be used for providing absorber member with heat absorption properties, for example, may include but are not limited to aluminum and its alloys, magnesium and it alloys and/or titanium and its alloys.

Absorber member 50 may be coupled with ultrasound transmission member 24 by any suitable means. In some embodiments, for example, absorber member 50 may be positioned at a desired location on transmission member 24 during manufacturing and then may be crimped, using a crimping device, to adhere to transmission member 24. Other methods for coupling absorber member 50 with transmission member 24 are also contemplated, such as pressure fitting, use of adhesive substances, and the like.

Absorber members 50 of the present invention are generally positioned on transmission member 24 at a location adjacent to the distal end of sonic connector 52. As shown in FIG. 3A, in some embodiments absorber member 50 is positioned immediately adjacent and abutting the distal end of sonic connector 52. In other embodiments, as in FIG. 3B, absorber member 50 may be disposed very close to the distal end of sonic connector 52 without actually abutting or touching sonic connector 52. In various embodiments, for example, the distance between the distal end of sonic connector 52 and the proximal end of absorber member 50 may range up to a few millimeters.

Figure 4C:
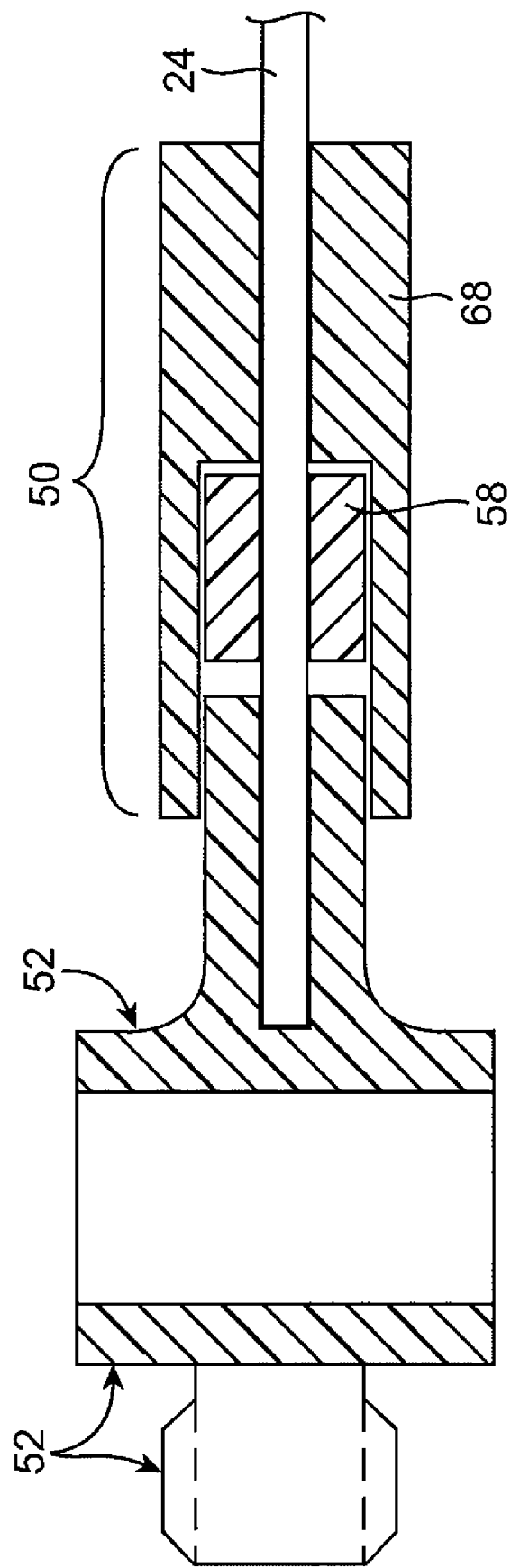

With reference now to FIGS. 4A and 4C, various embodiments of proximal end connector apparatus 12 may include an absorber member 50 having two or more component parts and/or comprising two or more different materials. For example, in some embodiments absorber member 50 includes a vibrational absorber 58 immediately surrounding transmission member 24 and a constraining member 56 immediately surrounding vibrational absorber 58. In various embodiments, vibrational absorber 58 and/or constraining member 56 may be configured to absorb transverse vibrations, absorb/transfer heat, or both. In some embodiments, for example, vibrational absorber 58 is made from a polymer or plastic capable of absorbing both vibrations and heat, while constraining member 56 is configured primarily to hold vibrational absorber 58 in place on transmission member 24.

In other embodiments, for example as in FIG. 4B, a differently shaped constraining member 64 may include one or more heat absorptive materials, and part of constraining member 64 may contact transmission member 24 or be disposed in close proximity to transmission member 24 to absorb heat generated in transmission member 24. Constraining member 64 may also absorb vibrations in some embodiments. In various embodiments, therefore, constraining member 56, 64 may serve a constraining function, a vibrational absorption function, a heat absorption function, or any combination thereof.

Referring now to FIG. 4C, another embodiment of absorber member 50 includes a constraining member 68 that overlaps a distal portion of sonic connector 52. Again, such a constraining member 68 may provide for vibration and/or heat absorption in addition to the constraining function. In such overlapping embodiments, vibrational absorber 58 may directly abut the distal end of sonic connector 52 or may be spaced apart from sonic connector 52, as shown in FIG. 4C. Generally, absorber members 50 of the invention will include at least one part that abuts or is closely adjacent to sonic connector 52, but may include one or more parts that are separate as well, as in FIG. 4C. As is evident from FIGS. 4A-4C, absorber member 50 may include any suitable combination of component parts having any suitable configuration and comprising any suitable combination of materials. In other embodiments, of course, absorber member 50 may comprise one, unitary piece, may comprise more than two components parts, or the like.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. An ultrasound catheter for disrupting occlusions in blood vessels, the ultrasound catheter comprising:
   an elongate flexible catheter body having a proximal end, a distal end and at least one lumen;
   an ultrasound transmission member extending longitudinally through the lumen of the catheter body;
   a sonic connector coupled with a proximal end of the ultrasound transmission member for coupling the ultrasound transmission member with a separate ultrasound generating device, the sonic connector comprising a proximal portion and a distal portion; and
   at least one absorber member coupled with the ultrasound transmission member adjacent the sonic connector,
   wherein the at least absorber member comprises at least two component parts, the component parts comprising:
     at least one vibrational absorber in contact with the transmission member for absorbing vibrations, wherein the vibrational absorber is disposed distally to the distal portion of the sonic connector; and
     at least one constraining member coupled with the vibrational absorber for holding the vibrational absorber in place on the transmission member, wherein the at least one constraining member comprises a proximal portion and a distal portion, and wherein the proximal portion of the constraining member overlaps the distal portion of the sonic connector.

2. An ultrasound catheter as in claim 1, wherein the absorber member surrounds a portion of the ultrasound transmission member adjacent a distal end of the sonic connector.

3. An ultrasound catheter as in claim 2, wherein the absorber member includes a bore for receiving the ultrasound transmission member.

4. An ultrasound catheter as in claim 3, wherein the absorber member is tubular.

5. An ultrasound catheter as in claim 1, wherein the absorber member contacts a distal end of the sonic connector.

6. An ultrasound catheter as in claim 1, wherein the absorber member is separated from a distal end of the sonic connector by a distance of approximately ¼ wavelength of an ultrasound wave transmitted to the ultrasound catheter.

7. An ultrasound catheter as in claim 1, wherein the at least one constraining member contacts the transmission member and comprises at least one absorptive material for absorbing heat.

8. An ultrasound catheter as in claim 7, wherein the at least one constraining member contacts a portion of the sonic connector.

9. An ultrasound catheter as in claim 1, wherein at least one of the vibrational absorber and the constraining member is capable of absorbing heat.

10. An ultrasound catheter as in claim 1, wherein the at least one constraining member comprises a bore for receiving the ultrasound transmission wire, wherein the bore includes a widened portion for receiving the vibrational absorber.

11. An ultrasound catheter as in claim 10, wherein the constraining member is tubular.

12. An ultrasound catheter as in claim 10, wherein the constraining member is coupled with at least one of the vibrational absorber and the ultrasound transmission wire by at least one of crimping, bonding, fusing or welding.

13. An ultrasound catheter as in claim 1, wherein the absorber member is capable of absorbing heat.

14. An ultrasound catheter as in claim 1, further comprising a heat absorbing member coupled with the ultrasound transmission member for absorbing heat.

15. An ultrasound catheter as in claim 1, wherein the absorber member comprises at least one vibration absorbing material selected from the group consisting of a rubber, a polymer, and a rubber/polymer combination.

16. An ultrasound catheter as in claim 15, wherein the absorber member further comprises at least one metal having heat conductivity properties.

17. An ultrasound catheter as in claim 16, wherein the at least one metal is selected from the group consisting of aluminum, aluminum alloys, titanium, titanium alloys, magnesium, and magnesium alloys.

18. An ultrasound catheter as in claim 1, wherein the absorber member is coupled with the ultrasound transmission wire by at least one of crimping, bonding, fusing or welding.

19. An ultrasound catheter as in claim 1, wherein the vibrational absorber comprises a proximal portion and a distal portion, and wherein the proximal portion of the vibrational absorber is disposed distally to the proximal portion of the constraining member and the distal portion of the vibrational absorber is disposed proximally to the distal portion of the constraining member.

20. An ultrasound catheter for disrupting occlusions in blood vessels, the ultrasound catheter comprising:
- an elongate flexible catheter body having a proximal end, a distal end and at least one lumen;
- an ultrasound transmission member extending longitudinally through the lumen of the catheter body, the ultrasound transmission member having a proximal end;
- a sonic connector coupled with the proximal end of the ultrasound transmission member for coupling the ultrasound transmission member with a separate ultrasound generating device, the sonic connector comprising a proximal portion and a distal portion, wherein the distal portion of the sonic connector contacts the ultrasound transmission member, and wherein the proximal portion of the sonic connector is attached to the ultrasound generating device; and
- at least one absorber member coupled with the ultrasound transmission member adjacent the sonic connector,
- wherein the at least one absorber member comprises at least two component parts, the component parts comprising:
  - at least one vibrational absorber in contact with the transmission member for absorbing vibrations; and
  - at least one constraining member coupled with the vibrational absorber for holding the vibrational absorber in place on the transmission member and for absorbing heat, wherein the at least one constraining member overlaps a portion of the sonic connector.

21. An ultrasound catheter as in claim 20, wherein the at least one constraining member contacts a portion of the sonic connector.

22. An ultrasound catheter as in claim 20, wherein the at least one constraining member comprises a bore for receiving the ultrasound transmission wire, wherein the bore includes a widened portion for receiving the vibrational absorber.

23. An ultrasound catheter as in claim 22, wherein the constraining member is tubular.

24. An ultrasound catheter as in claim 20, wherein the proximal portion of the sonic connector is disposed proximally to the proximal end of the ultrasound transmission member.

25. An ultrasound catheter as in claim 20, wherein the vibrational absorber comprises a proximal portion and a distal portion, and wherein the proximal portion of the vibrational absorber is disposed distally to the proximal portion of the constraining member and the distal portion of the vibrational absorber is disposed proximally to the distal portion of the constraining member.

* * * * *

UNITED STATES PATENT AND TRADEMARK OFFICE
CERTIFICATE OF CORRECTION

PATENT NO. : 7,621,929 B2  Page 1 of 1
APPLICATION NO. : 11/179829
DATED : November 24, 2009
INVENTOR(S) : Nita et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 867 days.

Signed and Sealed this

Twenty-sixth Day of October, 2010

David J. Kappos
*Director of the United States Patent and Trademark Office*